United States Patent [19]
Zimmer et al.

[11] Patent Number: 6,110,941
[45] Date of Patent: Aug. 29, 2000

[54] COMPOUNDS ANALOGOUS TO THALIDOMIDE FROM THE CLASS COMPRISING PIPERIDINE-2,6-DIONES

[75] Inventors: Oswald Zimmer, Wuerselen; Werner Winter, Aachen; Stephan Wnendt, Aachen; Kai Zwingenberger, Aachen; Kurt Eger, Tuebingen; Uwe Teubert, Oschatz, all of Germany

[73] Assignee: Gruenenthal GmbH, Aachen, Germany

[21] Appl. No.: 09/015,624

[22] Filed: Jan. 29, 1998

[30] Foreign Application Priority Data

Feb. 1, 1997 [DE] Germany .............................. 197 03 793

[51] Int. Cl.[7] ...................................................... A01N 43/40
[52] U.S. Cl. ............................................. 514/323; 546/221
[58] Field of Search ............................... 546/201; 514/323

[56] References Cited

U.S. PATENT DOCUMENTS

| | | | |
|---|---|---|---|
| 5,356,406 | 10/1994 | Ciganek et al. | 546/201 |
| 5,463,063 | 10/1995 | Muller | 546/201 |
| 5,480,892 | 1/1996 | Ciganek et al. | 546/201 |
| 5,698,579 | 12/1997 | Muller | 514/416 |

FOREIGN PATENT DOCUMENTS

| | | |
|---|---|---|
| 4211812A1 | 10/1992 | Germany . |
| WO92/14455 | 9/1992 | WIPO . |
| WO98/03502 | 12/1998 | WIPO . |

OTHER PUBLICATIONS

Muller et al., *J. Med. Chem.,* 39: 3238–40 (1996).

Teubert et al., *Arch. Pharm. Pharm. Med. Checm.,* 331: 7–12 (1998).

Chemical Abstracts 66: 94788a (1967).

Chemical Abstracts 123: 216835b (1995).

Chemical Abstracts 124: 45119r (1996).

Masuda et al., "Double–Masked Trial of Cyclosporin Versus Colchicine and Long–Term Open Study of Cyclosporin in Behcet's Disease", *The Lancet,* May 20, 1989, pp. 1093–1095.

G. Tappeiner, "Therapie des Lupus Erythematodes 1994", (Therapy of Lupus Erythematosus 1994), *H+G,* vol. 69, 1994, pp. 816–822.

*Primary Examiner*—John Kight
*Assistant Examiner*—Raymond Covington
*Attorney, Agent, or Firm*—Evenson, McKeown, Edwards & Lenahan, P.L.L.C.

[57] ABSTRACT

Compounds analogous to thalidomide from the class comprising piperidine-2,6-diones are described, as are a method of preparing them and their use in drugs.

13 Claims, No Drawings

COMPOUNDS ANALOGOUS TO THALIDOMIDE FROM THE CLASS COMPRISING PIPERIDINE-2,6-DIONES

This invention relates to compounds analogous to thalidomide from the class comprising piperidine-2,6-diones, to a method of preparing them, and to their use in drugs.

The excessive formation of the cytokinin TNF-α (tumour necrosis factor α) plays a central part in the pathogenesis of graft-versus-host syndrome, of multiple sclerosis, or transplant rejection, aphthous stomatitis, erythema nodosum leprosum, morbus Boeck, rheumatoid arthritis and a series of other diseases which are associated with inflammatory symptoms. One basis for the therapy of these diseases consists of the targeted suppression of the release of TNF-α by administering immunosuppressant or immunomodulating active ingredients, such as dexamethasone, pentoxifylline or thalidomide for example.

A distinction must be made, however, between indications which necessitate a general immunosuppression and those for which the advantages and disadvantages of immunosuppression have to be weighed up. In the treatment of aphthous stomatitis, thalidomide has been shown to be superior to classical immunosuppressants. Other examples of diseases in which thalidomide has exhibited good efficacy without resulting in a general immunosuppression include cutaneous lupus erythematosus (H+G 69, 816 to 822 (1994)), pyoderma gangrenosum and orogenital ulcers with morbus Behcet (The Lancet, 20.05.89, 1093 to 1095). The pathogenetic factors of these lesions, which are restricted to the skin and mucous membranes, are endogenous mediators which have effects on the endothelium and on circulating leukocytes. Under the influence of TNF-α and other cytokinins, there is a marked increase in the adhesiveness of the endothelium in relation to leukocytes, which makes a definitive contribution to the development of vasculitis. With systemic pathogens, the effect of thalidomide itself is restricted to the skin and mucous membranes, which necessitates (additional) immunosuppression. Examples thereof include systemic lupus erythematosus, which apart from dermal phenomena also causes life-threatening changes of the internal vessels, particularly of the kidneys; type II leprareaction, involving the eyes and/or the joints, as well as morbus Behget, involving the eyes and/or joints.

Substances which, like thalidomide, suppress this alteration of the endothelium, but which at the same time completely or partly block reactions of the specific cellular immune defense, can constitute an important advance in the therapy of said systemic pathogens. One key messenger substance of the cellular immune response is interleukin-2, on which the proliferation of antigen-specific lymphocytes depends.

When developing new drugs, one aim is therefore to put into effect the anti-inflammatory properties of thalidomide jointly with immunosuppressive active components which thalidomide on its own does not have in its clinical application.

The underlying object of the present invention was to develop compounds analogous to thalidomide from the class comprising piperidine-2,6-diones, which inhibit the inflammation-triggered release of TNF-α as well as the antigen-induced synthesis of interleukin-2.

It has been found that the compounds according to the invention fulfill the stated requirements.

The present invention therefore relates to piperidine-2,6-diones, which are substituted in positions 3 and 5, of general formula (I)

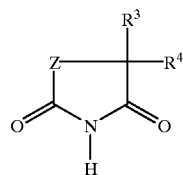

wherein Z represents one of the groups

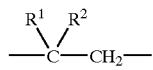

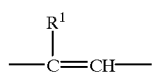

wherein the carbon atom with substituent $R^1$ is bonded to the carbonyl group, and in which $R^1$ denotes a phthalimide radical (when Z is —C($R^1R^2$)—CH$_2$—) or a phthalimide radical which is singly- or doubly-substituted with hydroxy, methoxy or amino groups (when Z represents —C($R^1$)=CH—), $R^2$ is hydrogen or a $C_1$–$C_6$ alkyl (straight chain or branched), $R^3$ represents hydrogen, a $C_1$–$C_6$ alkyl group (straight chain or branched), or an aromatic or heteroaromatic ring system, and $R^4$ denotes a $C_1$–$C_6$ alkyl group (straight chain or branched), or an aromatic or heteroaromatic ring system.

Of the piperidine-2,6-diones of formula (I), in which Z denotes —C($R^1R^2$)—CH$_2$—, $R^1$ denotes phthalimide and $R^2$ and $R^3$ denote hydrogen, the compound in which $R^4$ is phenyl is particularly preferred.

Of the piperidine-2,6-diones of formula (I), in which Z is —C($R^1$)=CH—, $R^3$ denotes ethyl and $R^4$ denotes phenyl, the compound in which $R^1$ is 3,4-dimethoxyphthalimide is particularly preferred.

The present invention further relates to a method of preparing compounds analogous to thalidomide from the class comprising piperidine-2,6-diones, of general formula (I). Compounds of general formula (I) where Z=—C($R^1R^2$)—CH$_2$—can be prepared by the condensation of phthalic anhydride with a substituted glutamic acid, such as 4-phenylglutamic acid or 4-methylglutamic acid for example, in an organic solvent, preferably pyridine, cyclisation of the product in acetic anhydride and subsequent conversion into the imide. Conversion of the anhydride into the imide is effected here by fusion with urea.

These target compounds of formula (I) can also be obtained by the reaction of phthalic anhydride with a 5-substituted 3-aminoglutarimide, preferably by heating in acetic acid.

Compounds of general formula (I) where Z=—C($R^1$)=CH—can be prepared by the condensation of a substituted phthalic anhydride, such as 3,4-dimethoxyphthalic anhydride for example, with 5-substituted 3-amino-3,4-dehydropiperidine-2,6-diones, such as 3-amino-5-ethyl-5-phenyl-glutaconimide for example, in an organic solvent, for example acetic acid.

EXAMPLE 1

2-(5-methyl-2,6-dioxo-piperidin-3-yl)- 1,3-dihydro-2H-isoindole- 1,3-dione (1)

2.00 g (11 mmoles) 4-methylglutamic acid and 1.95 g (13 mmoles) phthalic anhydride were heated for 6 hours under reflux in 15 ml of dry pyridine. After removing the solvent by distillation, the residue was heated to boiling for 1 hour in 10 ml acetic anhydride. The solid which precipitated on cooling was filtered off under suction and the filtrate was concentrated. After treating the filtrate with ether, the precipitate which formed was filtered off under suction and the purified precipitates were recrystallised from absolute toluene. 2.00 g (7 mmoles) of the crystalline material and 0.23 g (3.8 mmoles) urea were well mixed and were fused on an oil bath at about 200° C. for 30 minutes. The solidified melt was heated briefly to boiling, with 4 ml acetic anhydride and 6 ml ethanol in succession. The precipitated solid was filtered off under suction and recrystallised from DMF/water. 1.35 g (67% theoretical) 2-(5-methyl-2,6-dioxo-piperidin-3-yl)-1,3-dihydro-2H-isoindole-1,3-dione (1) were obtained, with a melting point of 270 to 272° C.

EXAMPLE 2

2-(5-phenyl-2,6-dioxo-piperidin-3-yl)-1,3-dihydro-2H-isoindole-1,3-dione (2)

3.00 g (12 mmoles) 4-phenylglutamic acid and 2.12 g (14 mmoles) phthalic anhydride were heated for 6 hours under reflux in 40 ml of dry pyridine. After removing the solvent by distillation, the residue was taken up in 50 ml of 5% HCl and extracted with ethyl acetate. The organic phase was washed with water, decolourised with activated carbon and dried over sodium sulphate. After removing the solvent by distillation, the residue was heated under reflux for 1 hour in 40 ml acetic anhydride. The solution was subsequently concentrated and treated with ether. The precipitate formed was filtered off under suction and was recrystallised from dry toluene. 2.00 g (6 mmoles) of the crystalline material and 0.19 g (3 mmoles) urea were fused on an oil bath at about 200° C. for 30 minutes. The solidified melt was heated briefly to boiling, with 4 ml acetic anhydride and 8 ml ethanol in succession. The precipitated solid was recrystallised from DMF/water. 0.80 g (40% theoretical) 2-(5-phenyl-2,6-dioxo-piperidin-3-yl)-1,3-dihydro-2H-isoindole-1,3-dione (2) were obtained, with a melting point of 228 to 231° C.

EXAMPLE 3

2-(5-ethyl-5-phenyl-2,6-dioxo-piperidin-3-yl)-1,3-dihydro-2H-isoindole-1,3-dione (3)

1.00 g (4 mmoles) 3-amino-5-ethyl-5-phenyl-glutaconimide were dissolved in 40 ml of anhydrous ethanol, and the solution was treated with 0.1 g of palladinised charcoal (10% Pd/C) and stirred for 8.5 hours in a hydrogen atmosphere. The solution was subsequently filtered from the catalyst and the filtrate was evaporated to dryness. The residue was heated for 4 hours under reflux with 0.70 g (5 mmoles) phthalic anhydride in 40 ml glacial acetic acid. After removing the solvent by distillation, the residue was recrystallised from ethanol. 0.99 g (63% theoretical) 2-(5-ethyl-5-phenyl-2,6-dioxo-piperidin-3-yl)-1,3-dihydro-2H-isoindole-1,3-dione (3) were obtained, with a melting point of 174–177° C.

EXAMPLE 4

2-(5-ethyl-5-phenyl-2,6-dioxo-1,2,5,6-tetrahydropyridin-3-yl)-4,5-dimethoxy-1,3-dihydro-2H-isoindole-1,3-dione (4)

0.45 g (2 mmoles) 3-amino-5-ethyl-5-phenyl-glutaconimide and 0.45 g (2 mmoles) 4,5-dimethoxyphthalic anhydride were heated for 5 hours under reflux in 15 ml glacial acetic acid. The solution was subsequently evaporated to dryness and the residue was recrystallised from ethanol. 0.55 g (67% theoretical) 2-(5-ethyl-5-phenyl-2,6-dioxo-1,2,5,6-tetrahydropyridin-3-yl)-4,5-dimethoxy-1,3-dihydro-2H-isoindole-1,3-dione(4) were obtained, with a melting point of 203–205° C.

The compounds according to the invention are toxicologically harmless and are therefore suitable as pharmaceutical active ingredients. Accordingly, the present invention also relates to the use of compounds analogous to thalidomide from the class comprising piperidine-2,6-diones, of general formula (I), as active ingredients in drugs, preferably as suppressors of the inflammation-triggered release of TNF-α and of the antigen-induced synthesis of interleukin-2.

In addition to at least one compound of general formula (I), drugs according to the invention contain support materials, fillers, solvents, diluents, colorants and/or binders. The selection of these adjuvant substances and of the amounts to be used depends on whether the drug is to be administered orally, intravenously, intraperitoneally, intradermally, intramuscularly, intranasally, buccally or locally. Preparations in the form of tablets, lozenges, dragees, capsules, granules, drops, juices or syrups are suitable for oral administration, and solutions, suspensions, readily reconstitutable dry preparations and sprays are suitable for parenteral and topical administration and for administration by inhalation. Compounds according to the invention in a deposit in dissolved form, in a carrier film or in a patch, optionally with the addition of agents which promote dermal penetration, are examples of suitable percutaneous forms of application. The compounds according to the invention can be released in a delayed manner from forms of preparations which can be employed orally or percutaneously.

The amount of active ingredient to be administered to the patient depends on the weight of the patient, on the type of application, on the indication and on the degree of severity of the illness. 1 to 150 mg/kg of at least one compound analogous to thalidomide of formula (I) is usually administered.

Pharmacological Investigations

The release of TNF-α can be investigated in vitro on human mononuclear cells of the peripheral blood (T cells, B cells and monocytes), after stimulation with lipopolysaccharide (LPS). LPS is a constituent of the bacterial cell wall and stimulates monocytes and macrophages.

Apart from stimulation with LPS, the release of TNF-α can also be provoked by the stimulation of human mononuclear cells of the peripheral blood by T cells of monoclonal antibodies which react specifically with activation antigens (antiCD2-antiCD28) or by the bacterial antigen toxic shock syndrome toxin-1 TSST-1. Apart from the release of TNF-α, these stimulants result, amongst other effects, in the formation of interleukin-2 (Il-2).

LPS Stimulation of Mononuclear Cells: Effect on TNF-α

The release of TNF-α can be investigated in vitro on human mononuclear cells of the peripheral blood, namely T cells, B cells and monocytes, after stimulation with lipopolysaccharide (LPS). LPS is a constituent of the bacterial cell wall and stimulates monocytes and macrophages.

Mononuclear cells were obtained from the heparin-treated blood of at least three volunteer donors. For this purpose, 20 ml blood in each case were separated by known methods via a Ficoll-Paque gradient, and the cells were harvested and washed three times with a cell culture medium. This cell culture medium consisted of RPMI 1640 medium, supplemented with 2 mM glutamine (Life Technologies, Eggenstein), 10% foetal calf serum (Life Technologies), 50 µg/l streptomycin (Sigma, Deisenhofen), 50 IU/ml penicillin (Sigma) and 100 µM β-mercaptoethanol (Merck, Darmstadt). The cells were finally taken up in 15 ml cell culture medium and were divided into 1 ml batches in sterile 24-hole incubation plates (Sigma). 1 µl dimethylsulphoxide (DMSO, Merck) or 1 µl of a solution of the test substance (in DMSO; final concentration in the test: 0.5; 5; 12.5 and 50 µg/ml) was added to each of the 1 batches and the batches were incubated for one hour in a $CO_2$ incubation cabinet (5% $CO_2$, 90% atmospheric humidity). 2.5 µg LPS (from E. coli 0127: B8, Sigma) was subsequently added to each batch with the exception of the controls. Incubation of the cultures was continued for 20 hours. Following the tests, the of TNF-α in the cell culture supernatant liquors was determined using commercial ELISA tests (Boehringer Mannheim). The magnitude of the TNF-α inhibition was calculated from the measured values of the control batches which were not treated with active ingredient and from the batches incubated with the test compounds. The concentrations which resulted in 50% inhibition of the release of TNF-α (the IC50 values) were calculated by means of linear regression analysis.

Table 1 the inhibiting effect of the compounds according to the invention on the LPS-induced release of TNF-α:

TABLE 1

| Example No. | Inhibition of the release of TNF-α (in %) at a final concentration of 50 µg/ml in the test | $IC_{50}$ [µg/ml] |
|---|---|---|
| 1 | 48% | not determined |
| 2 | 69% | 8.7 |
| 3 | 80% | 11.0 |
| 4 | 90% | 2.0 |

Stimulation of T Cells: Inhibition of Il-2

The release of interleukin-2 can be investigated by the in vitro stimulation of human mononuclear cells of the peripheral blood, which in addition to T cells also contains B cells and monocytes. By polyclonal stimulation via constant epitopes of the T cell receptor or via what are termed accessory signal-transmitting surface molecules, a measurable range is obtained which is more pronounced than that from the antigen stimulation of smaller T cell populations. A combination of two such accessory signals was used, namely those transmitted via surface molecules CD2 and CD28.

Mononuclear cells were obtained from the heparin-treated blood of at least three volunteer donors. For this purpose, 20 ml blood in each case were separated by known methods via a Ficoll-Paque gradient, and the cells were harvested and washed three times with a cell culture medium. This cell culture medium consisted of RPMI 1640 medium, supplemented with 2 mM glutamine (Life Technologies, Eggenstein), 10% fetal calf serum (Life Technologies), 50 µg/l streptomycin (Sigma, Deisenhofen), 50 IU/ml penicillin (Sigma) and 100 µM β-mercaptoethanol (Merck, Darmstadt). The mononuclear cells were finally taken up in 15 ml cell culture medium and were divided into 1 ml batches in sterile 24-hole incubation plates (Sigma). 1 µl dimethylsulphoxide (DMSO, Merck) or 1 µl of a solution of the test substance (in DMSO; final concentration in the test: 0.5; 5; 12.5 and 50 µg/ml) was added to each of the 1 ml batches and the batches were incubated for one hour in a $CO_2$ incubation cabinet (5% $CO_2$, 90% atmospheric humidity). 0.1 µg/ml of monoclonal antibodies (clone no. AICD2.M1 from Prof. Dr. Meuer; anti-CD28 from CLB, Amsterdam) was subsequently added to each batch with the exception of the controls. Incubation of the cultures was continued for 20 hours. Following the tests, the concentration of Il-2 in the cell culture supernatant liquors was determined using commercial ELISA tests (Boehringer Mannheim). The magnitude of the Il-2 inhibition was calculated from the measured values of the control batches which were not treated with active ingredient and from the batches incubated with the test compounds.

Under these conditions, at a concentration of 50 µg/ml, the substance from example 4 inhibited the CD2/CD28-stimulated synthesis of Il-2 by 86±6%. When using staphylococcus superantigen (from E. Coli 0127: B8; Sigma, Deisenhofen) TSST-1 (0.1 µg/ml) as a T cell stimulus, the Il-2 synthesis was inhibited by 77±20%.

The above investigations show that compounds analogous to thalidomide from the class comprising piperidine-2,6-diones of formula (I) inhibit both the inflammation-triggered release of TNF-α and the antigen-induced synthesis of interleukin-2.

What is claimed is:
1. A substituted piperidine-2,6-dione corresponding to formula I:

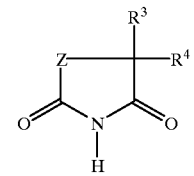

wherein

Z denotes —C($R^1R^2$)—$CH_2$— or —C($R^1$)=CH—, $R^1$ represents phthalimide when Z=—C($R^1R^2$)—$CH_2$—, or a phthalimide group which is singly- or doubly-substituted with hydroxy, methoxy or amino groups when Z=—C($R^1$)=CH—, $R^2$ denotes hydrogen or a $C_1$–$C_6$ alkyl group, $R^3$ is hydrogen, a $C_1$–C6 alkyl group or an aromatic or heteroaromatic ring system, and $R^4$ represents a $C_1$–$C_6$ alkyl group or an aromatic or heteroaromatic ring.

2. A substituted piperidine-2,6-dione according to claim 1, wherein

Z is —C($R^1R^2$)—$CH_2$, $R^1$ denotes phthalimide, $R^2$ represents hydrogen, $R^3$ denotes hydrogen or ethyl, and $R^4$ represents methyl or phenyl.

3. A substituted piperidine-2,6-dione according to claim 1, wherein

Z is —C($R^1$)=CH—, $R^1$ denotes 3,4-dimethoxyphthalimide, $R^3$ represents ethyl, and $R^4$ represents phenyl.

4. A method of preparing substituted piperidine-2,6-dione corresponding to the formula:

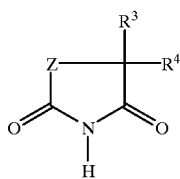

wherein
Z is —C(R$^1$R$^2$)—CH$_2$,
R$^1$ denotes phthalimide,
R$^2$ represents hydrogen,
R$^3$ denotes hydrogen or ethyl, and
R$^4$ represents methyl or phenyl;
said method comprising the steps of:
  condensing a phthalic anhydride with a substituted glutamic acid to form a condensation product,
  cyclizing the condensation product to form an anhydride, and
  converting the anhydride into an imide.

5. A method of preparing a substituted piperidine-2,6-dione corresponding to formula I:

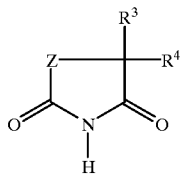

wherein
Z is —C(R$^1$)=CH—,
R$^1$ denotes 3,4-dimethoxyphthalimide,
R$^3$ represents ethyl, and
R$^4$ represents phenyl;
said method comprising the step of condensing a phthalic anhydride with a substituted 3-aminoglutaconimide or a 5-substituted 3-aminoglutarimide.

6. A pharmaceutical composition comprising a substituted piperidine-2,6-dione corresponding to formula I:

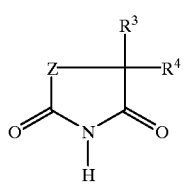

wherein
Z denotes —C(R$^1$R$^2$)—CH$_2$— or —C(R$^1$)=CH—,
R$^1$ represents phthalimide when Z=—C(R$^1$R$^2$)—CH$_2$—, or a phthalimide group which is singly- or doubly-substituted with hydroxy, methoxy or amino groups when Z=—C(R$^1$)=CH—,
R$^2$ denotes hydrogen or a C$_1$–C$_6$ alkyl group,
R$^3$ is hydrogen, a C$_1$–C$_6$ alkyl group or an aromatic or heteroaromatic ring system, and
R$^4$ represents a C$_1$–C$_6$ alkyl group or an aromatic or heteroaromatic ring and at least one pharmaceutical carrier or adjuvant.

7. A pharmaceutical composition according to claim 6, wherein
Z is —C(R$^1$R$^2$)—CH$_2$,
R$^1$ denotes phthalimide,
R$^2$ represents hydrogen,
R$^3$ denotes hydrogen or ethyl, and
R$^4$ represents methyl or phenyl.

8. A pharmaceutical composition according to claim 6, wherein
Z is —C(R$^1$)=CH—,
R$^1$ denotes 3,4-dimethoxyphthalimide,
R$^3$ represents ethyl, and
R$^4$ represents phenyl.

9. A method of modulating the immune response of a mammal, said method comprising administering to said mammal an effective immunomodulating amount of a substituted piperidine-2,6-dione corresponding to formula I:

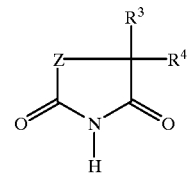

wherein
Z denotes —C(R$^1$R$^2$)—CH$_2$— or —C(R$^1$)=CH—,
R$^1$ represents phthalimide when Z=—C(R$^1$R$^2$)—CH$_2$—, or a phthalimide group which is singly- or doubly-substituted with hydroxy, methoxy or amino groups when Z=—C(R$^1$)=CH—,
R$^2$ denotes hydrogen or a C$_1$–C$_6$ alkyl group,
R$^3$ is hydrogen, a C$_1$–C$_6$ alkyl group or an aromatic or heteroaromatic ring system, and
R$^4$ represents a C$_1$–C$_6$ alkyl group or an aromatic or heteroaromatic ring.

10. A method according to claim 9, wherein
Z is —C(R$^1$R$^2$)—CH$_2$,
R$^1$ denotes phthalimide,
R$^2$ represents hydrogen,
R$^3$ denotes hydrogen or ethyl, and
R$^4$ represents methyl or phenyl.

11. A method according to claim 9, wherein
Z is —C(R$^1$)=CH—,
R$^1$ denotes 3,4-dimethoxyphthalimide,
R$^3$ represents ethyl, and
R$^4$ represents phenyl.

12. A method for inhibiting antigen-induced synthesis of interleukin-2 in a mammal, comprising administering to said mammal an effective amount of a substituted piperidine-2,6-dione corresponding to formula I:

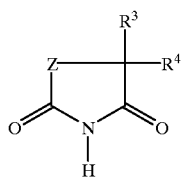

wherein

Z denotes —C($R^1R^2$)—$CH_2$— or —C($R^1$) CH—, $R^1$ represents phthalimide when Z=—C($R^1R^2$)—$CH_2$—, or a phthalimide group which is singly- or doubly-substituted with hydroxy, methoxy or amino groups when Z=—C($R^1$)=CH—, $R^2$ denotes hydrogen or a $C_1$–$C_6$ alkyl group, $R^3$ is hydrogen, a $C_1$–$C_6$ alkyl group or an aromatic or heteroaromatic ring system, and $R^4$ represents a $C_1$–$C_6$ alkyl group or an aromatic or heteroaromatic ring.

13. A substituted piperidine-2,6-dione corresponding to formula I:

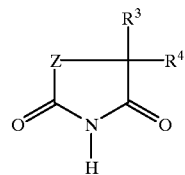

wherein

Z is —C($R^1$)=CH—, $R^1$ is a phthalimide group which is singly- or doubly-substituted with amino groups, $R^3$ is a $C_1$–$C_6$ alkyl group, and $R^4$ is a $C_1$–C6 alkyl group.

* * * * *